US006482836B1

(12) United States Patent
Huang et al.

(10) Patent No.: US 6,482,836 B1
(45) Date of Patent: Nov. 19, 2002

(54) CRF ANTAGONISTIC QUINO- AND QUINAZOLINES

(76) Inventors: Charles Huang, 12341 Goldfish Ct., San Diego, CA (US) 92129; Keith M. Wilcoxen, 3620 3rd Ave. 105, San Diego, CA (US) 92103; Chen Chen, 13922 Sparren Ave., San Diego, CA (US) 92129; Mustapha Haddach, 5942 Rancho Mission Rd. 136, San Diego, CA (US) 92108; James R. McCarthy, 401 Loma Larga, San Diego, CA (US) 92075

( * ) Notice: Subject to any disclaimer, the term of this patent is extended or adjusted under 35 U.S.C. 154(b) by 0 days.

(21) Appl. No.: 09/403,393

(22) PCT Filed: Apr. 15, 1998

(86) PCT No.: PCT/EP98/02267

§ 371 (c)(1),
(2), (4) Date: Oct. 19, 1999

(87) PCT Pub. No.: WO98/47874

PCT Pub. Date: Oct. 29, 1998

Related U.S. Application Data

(60) Provisional application No. 60/044,525, filed on Apr. 22, 1997.

(51) Int. Cl.[7] .................. A61K 31/4706; C07D 215/00; C07D 215/42; C07D 215/12
(52) U.S. Cl. ................. 514/313; 514/314; 514/311; 546/159; 546/152; 546/176
(58) Field of Search ............... 514/313, 311, 514/314; 546/159, 152, 176

(56) References Cited

FOREIGN PATENT DOCUMENTS

| WO | WO 95/33750 | 12/1995 |
|---|---|---|
| WO | WO 96/35689 | 11/1996 |
| WO | WO 98/08846 | 3/1998 |
| WO | 9808846 | * 3/1998 |
| WO | WO 98/29397 | 7/1998 |

OTHER PUBLICATIONS

Olis W.D. "Synthesis of Heterocyl . . . "; J.R.C. Perkin Transactions 1,953–956 (1989).*
Michne et al "Novel Inhibitors of Potassium Ion Channels . . . "; J.Med.Chem.38, 1877–83(1995).*
J.B.Wommack et al(Potential Antimalarials;J.Med.Chem. 14/12/1218–1220(1971).*
Schroeder et al.; "Non–steroidal antiinflammatory agents. IV . . . "; Eur.J.Med.Chem.–Chim.Ter. 14/6, 499–506(1979).*
Ollis, David W.,"Heterocyclic Mesomeric Betaines", J. Chem. Soc. Perkin Trans. (1989) pp. 953–956.
Womack J.B. et al., "Potential Antimalarials", Journal of Medicinal Chemistry, (1971) vol. 14. No. 12, pp. 1218–1220.
Michne, William F., "Novel Inhibitors of Potassium Iion Channels on Human T Lymphocytes", J. Med. Chem., (1995), 38:1877–1883.
Ollis et al."JCS Pekin Tran.",Heterocyclic . . . Part 2.Synthesis . . . , 1/5,953–6, May 1989.*

\* cited by examiner

Primary Examiner—Mukund J. Shah
Assistant Examiner—Sudhaker B. Patel
(74) Attorney, Agent, or Firm—Scully, Scott, Murphy & Presser

(57) ABSTRACT

This invention concerns compounds of formula

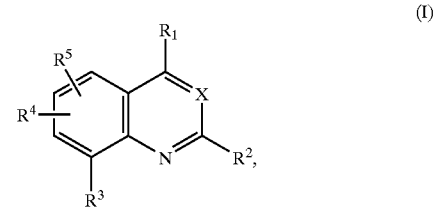

(I)

including the stereoisomers and the pharmaceutically acceptable acid addition salt forms thereof, wherein $R^1$ is $C_{1-6}$alkyl, $NR^6R^7$, $OR^6$ or $SR^7$; $R^2$ is hydrogen, $C_{1-6}$alkyl, $C_{1-6}$alkyloxy or $C_{1-6}$alkylthio; $R^3$ is $Ar^1$ or $Het^1$; $R^4$ and $R^5$ are each independently selected from hydrogen, halo, $C_{1-6}$alkyl, $C_{1-6}$alkyloxy, trifluoromethyl, cyano, nitro, amino, and mono- or di($C_{1-6}$alkyl)amino; $R^6$ is hydrogen, $C_{1-6}$alkyl, $C_{1-6}$alkylsulfonyl, $C_{1-6}$alkylsulfoxy or $C_{1-6}$alkylthio; $R^7$ is hydrogen, $C_{1-8}$alkyl, mono- or di($C_{3-6}$cycloalkyl)methyl, $C_{3-6}$cycloalkyl, $C_{3-6}$alkenyl, hydroxy $C_{1-6}$alkyl, $C_{1-6}$alkylcarbonyloxy-$C_{1-6}$alkyl or $C_{1-6}$alkyloxy$C_{1-6}$alkyl; $R^6$ is $C_{1-8}$alkyl, mono- or di($C_{3-6}$cycloalkyl)-methyl, $Ar^2CH_2$, $C_{1-6}$alkyloxy$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, mono- or di($C_{1-6}$alkyl)amino$C_{1-6}$alkyl, di($C_{1-6}$alkyl)amino, $C_{1-6}$alkylcarbonyl$C_{1-6}$alkyl; or $R^6$ and $R^7$ taken together with the nitrogen atom to which they are attached may form a pyrrolidinyl, piperidinyl, homopiperidinyl or morpholinyl group, optionally substituted with $C_{1-6}$alkyl or $C_{1-6}$alkyloxy$C_{1-6}$alkyl; and $Ar^1$ and $Ar^2$ are each optionally substituted phenyl; and $Het^1$ is optionally substituted pyridinyl; having CRF receptor antagonistic properties; pharmaceutical compositions containing such compounds as active ingredients; methods of treating disorders related to hypersecretion of CRF such as depression, anxiety, substance abuse, by administering an effective amount of a compound of formula (I).

14 Claims, No Drawings

CRF ANTAGONISTIC QUINO- AND QUINAZOLINES

RELATED APPLICATIONS

This application is claiming benefit of PCT Patent Application No. PCT/EP98/02267, filed on Apr. 15, 1998, which, in turn, is claiming priority of U.S. Provisional Patent Application Ser. No. 60/044,525, filed on Apr. 22, 1997.

BACKGROUND OF THE INVENTION

This invention relates to quino- and quinazolines which possess CRF receptor antagonistic properties, to pharmaceutical compositions containing these compounds as active ingredient, and the use thereof in the treatment of endocrine, psychiatric and neurologic conditions or illnesses, including stress-related disorders in general.

The first corticotropin-releasing factor (CRF) was isolated from ovine hypothalmi and identified as a 41-amino acid peptide (Vale et al., *Science* 213:1394–1397, 1981). Subsequently, sequences of human and rat CRF were isolated and determined to be identical, but different from ovine CRF in 7 of the 41 amino acid residues (Rivier et al., *Proc. Natl. Acad. Sci. USA* 80:4851, 1983; Shibahara et al., *EMBO J.* 2:775, 1983). CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., *Science* 213:1394–1397, 1981). Briefly, CRF is believed to initiate its biological effects by binding to a plasma membrane receptor which has been found to be distributed throughout the brain (DeSouza et al., *Science* 221:1449–1451, 1984), pituitary (DeSouza et al., *Methods Enzymol.* 124:560, 1986; Wynn et al., *Biochem. Biophys. Res. Comm.* 110:602–608, 1983), adrenals (Udelsman et al., *Nature* 319:147–150, 1986) and spleen (Webster, E. L., and E. B. DeSouza, *Endocrinology* 122:609–617, 1988). The CRF receptor is coupled to a GTP-binding protein (Perrin et al., *Endocrinology* 118: 1171–1179, 1986) which mediates CRF-stimulated increase in intracellular production of cAMP (Bilezikjian, L. M., and W. W. Vale, *Endocrinology* 113:657–662, 1983).

In addition to its role in stimulating the production of ACTH and POMC, CRF is also believed to coordinate many of the endocrine autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555–2564, 1992; Sapolsky et al., *Science* 238:522–524, 1987; Tilders et al., *Regul. Peptides* 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 2/8332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J. Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J. Physiol.* 255:R744, 1988). Furthermore, clinical data suggest that CRF may be hypersecreted in the brain in depression, anxiety-related disorders, and anorexia nervosa. (DeSouza, *Ann. Reports in Med. Chem.* 25:215–223, 1990).

Accordingly, clinical data suggest that CRF receptor antagonists may represent novel antidepressant and/or anxiolytic drugs that may be useful in the treatment of the neuropsychiatric disorders manifesting hypersecretion of CRF.

Due to the physiological significance of CRF, the development of further biologically active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

CRF receptor antagonists have been reported in for example, WO-94/13676, WO-94/13677, WO-95/33750 and WO-96/35689 which disclose pyrrolopyrimidines, pyrazolo [3,4-d]pyrimidines and substituted purines as CRF receptor antagonists. Aminoquinoline derivatives are described in Michne W. F. et al. *J. Med. Chem.*, 38:2748–2762, 1995, as intermediates for 4-substituted-1,4-dihydroquinolines. German patent DE-2,909,871 discloses substituted quinolines as useful intermediates in the synthesis of nitriles. Other structurally related quinoline derivatives are described in Schroeder E. et al. *Eur. J. Med. Chem.—Chim. Ther.*, 14:499–506, 1979, as non-steroidal antiinflammatory agents and in Wommack J. B. et al. *J. Med. Chem.*, 14:1218–1220, 1971, as antimalarials. Ollis W. D. et al. *J. C. S. Perkin Trans.* 1, 953–956, 1989, discloses 2,4-dimethyl-8-(2-nitrophenyl)-quinoline as an intermediate in the synthesis of heterocyclic betaines. 2,4-Diaminoquinazolines are known from WO-94/18980 having insecticidal activity.

The compounds of the present invention differ from the cited art-known compounds structurally, by the nature of the substituents on the quinoline or quinazoline moiety, and pharmacologically by the fact that, unexpectedly, these compounds have CRF antagonistic properties.

DESCRIPTION OF THE INVENTION

This invention concerns CRF antagonistic compounds of formula (I)

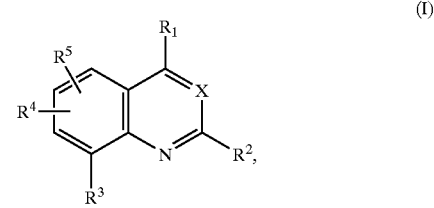

including the stereoisomers and the pharmaceutically acceptable acid addition salt forms thereof, wherein X is N or CH;

$R^1$ is $C_{1-6}$alkyl, $NR^6R^7$, $OR^7$ or $SR^7$;

in case X is N then $R^2$ is hydrogen, $C_{1-6}$alkyl, $C_{1-6}$alkyloxy or $C_{1-6}$alkylthio;

in case X is CH then $R^2$ is $C_{1-6}$alkyl, $C_{1-6}$alkyloxy or $C_{1-6}$alkylthio;

$R^3$ is $Ar^1$ or $Het^1$;

$R^4$ and $R^5$ are each independently selected from hydrogen, halo, $C_{1-6}$alkyl, $C_{1-6}$alkyloxy, trifluoromethyl, cyano, nitro, amino, and mono- or di($C_{1-6}$alkyl)amino;

$R^6$ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy$C_{1-6}$alkyl;

$R^7$ is $C_{1-8}$alkyl, mono- or di($C_{3-6}$cycloalkyl)methyl, $Ar^2CH_2$, $C_{1-6}$alkyloxy$C_{1-6}$alkyl hydroxy$C_{1-6}$alkyl, $C_{3-6}$alkenyl, thienylmethyl, furanylmethyl, $C_{1-6}$alkylthio$C_{1-6}$alkyl, mono- or di($C_{1-6}$alkyl)amino$C_{1-6}$alkyl, di($C_{1-6}$alkyl)amino, $C_{1-6}$alkylcarbonyl$C_{1-6}$alkyl;

or $R^6$ and $R^7$ taken together with the nitrogen atom to which they are attached may form a pyrrolidinyl, piperidinyl, homopiperidinyl or morpholinyl group, optionally substituted with $C_{1-6}$alkyl or $C_{1-6}$alkyloxy$C_{1-6}$alkyl; and $Ar^1$ is phenyl; phenyl substituted with 1, 2 or 3 substituents each independently selected from halo, $C_{1-6}$alkyl, trifluoromethyl, hydroxy, cyano, $C_{1-6}$alkyloxy, benzyloxy, $C_{1-6}$alkylthio, nitro, amino and mono- or di($C_{1-6}$alkyl)amino;

$Het^1$ is pyridinyl; pyridinyl substituted with 1, 2 or 3 substituents each independently selected from halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl)amino; and $Ar^2$ is phenyl; phenyl substituted with 1, 2 or 3 substituents each independently selected from halo, $C_{1-6}$alkyl, $C_{1-6}$alkyloxy, di($C_{1-6}$alkyl)amino$C_{1-6}$alkyl, trifluoromethyl.

In a further aspect the invention concerns novel compounds of formula (I) as defined above, with the proviso that 2,4-dimethyl-8-(2-nitrophenyl)-quinoline is not included.

This proviso is intended to exclude said quinoline compound which has been disclosed by Ollis W. D. et al. in *J. C. S. Perkin Trans.* 1, (5), 953–956 (1989).

As used in the foregoing definitions and hereinafter, halo is generic to fluoro, chloro, bromo and iodo; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; $C_{1-2}$alkyl defines straight saturated hydrocarbon radicals having from 1 to 2 carbon atoms such as methyl and ethyl; $C_{2-4}$alkyl defines straight and branched chain saturated hydrocarbon radicals having from 2 to 4 carbon atoms such as ethyl, propyl, butyl, 1-methylethyl and the like; $C_{3-4}$alkyl defines straight and branched chain saturated hydrocarbon radicals having from 3 to 4 carbon atoms such as propyl, butyl, 1-methylethyl and the like; $C_{1-6}$alkyl includes $C_{1-2}$alkyl and $C_{3-4}$alkyl radicals as defined hereinbefore and the higher homologues thereof having from 5 to 6 carbon atoms such as, pentyl, the pentyl isomers, hexyl and the hexyl isomers; $C_{1-8}$alkyl includes $C_{1-6}$alkyl and the higher homologues thereof having from 7 to 8 carbon atoms such as, for example, heptyl, octyl and the like; $C_{3-6}$alkenyl defines straight and branched chain hydrocarbon radicals containing one double bond and having from 3 to 6 carbon atoms such as, for example, 2-propenyl, 3-butenyl, 2-pentenyl, 3-pentenyl, 3-methyl-2-butenyl, and the like; and where said $C_{3-6}$alkenyl is linked to a nitrogen or oxygen, the carbon atom making the link preferably is saturated. $C_{3-6}$cycloalkyl comprises cyclopropyl, cyclobutyl, cyclopentyl and cyclohexyl. Hydroxy$C_{1-6}$alkyl refers to $C_{1-6}$alkyl substituted with a hydroxy group.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention. For instance, compounds of formula (I) wherein $Het^1$ is pyridinyl substituted with hydroxy, may exist in their corresponding tautomeric form.

Whenever used hereinafter, the term "compounds of formula (I)" is meant to include also the pharmaceutically acceptable acid addition salts and all stereoisomeric forms.

The numbering of the bicyclic ring-system present in the compounds of formula (I) is shown below:

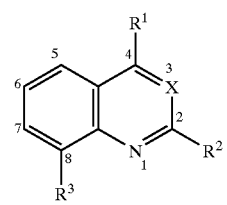

Particular groups of compounds within the invention are those compounds of formula (I) wherein one or more of the radicals have the following meaning:

a) $R^1$ is $NR^6R^7$ wherein $R^6$ is hydrogen or $C_{1-8}$alkyl; in particular $C_{2-4}$alkyl; and $R^7$ is $C_{1-8}$alkyl or $C_{3-6}$cycloalkylmethyl; in particular $C_{2-4}$alkyl or cyclopropylmethyl;

b) $R^1$ is $OR^7$ or $SR^7$ wherein $R^7$ is $C_{1-6}$alkyl; in particular $C_{1-4}$alkyl;

c) $R^2$ is $C_{1-6}$alkyl; in particular $C_{1-2}$alkyl;

d) $R^3$ is a phenyl substituted with 1, 2 or 3 substituents each independently selected from $C_{1-6}$alkyl, $C_{1-6}$alkyloxy or halo; wherein the phenyl moiety is preferably substituted in the 3-, 4-, 6-, 2,4- or 2,4,6- positions; or $R^3$ is a pyridinyl substituted with 1, 2 or 3 substituents each independently selected from halo, amino, nitro, trifluoromethyl, mono- or di($C_{1-6}$alkyl) amino, or $C_{1-6}$alkyl; wherein the pyridinyl moiety preferably is connected via the 2- or 3-position to the remainder of the molecule; and e) $R^4$ and $R^5$ are each independently selected from hydrogen or $C_{1-6}$alkyl.

Preferred compounds are those compounds of formula (I) wherein $R^1$ is $NR^6R^7$ and $R^6$ is $C_{3-4}$alkyl, preferably propyl; $R^7$ is $C_{3-4}$alkyl or cyclopropylmethyl, preferably propyl; $R^2$ is methyl; $R^3$ is a phenyl substituted with 1, 2 or 3 substituents each independently selected from halo, methyl or methoxy; or $R^3$ is pyridinyl substituted with 1, 2 or 3 substituents each independently selected from halo, methyl or dimethylamino; and $R^4$ and $R^5$ are hydrogen.

More preferably $R^3$ is phenyl substituted on the 2- and 4-position with $C_{1-2}$alkyl or halo; in particular $R^3$ is 2,4-dichlorophenyl.

The most preferred compounds of formula (I) are
2-methyl-4-dipropylamino-8-(2',4'-dichlorophenyl)-quinoline; and
2-methyl-4-(N-propyl-N-cyclopropanemethyl)amino-8-(2',4'-dichlorophenyl)-quinoline; the stereoisomeric forms and the pharmaceutically acceptable acid addition salts thereof.

The compounds of the present invention can generally be prepared by reacting an intermediate of formula (IV), wherein Z is bromo or iodo, with an intermediate of formula (V) under Suzuki coupling conditions. Appropriate Suzuki coupling conditions are for example, stirring a solution of an intermediate (I) and a tetrakis(triphenylphosphine) palladium catalyst in a reaction-inert solvent, e.g. toluene, in the presence of an appropriate base, e.g. sodium carbonate, while adding intermediate (V) dissolved in an alcohol, e.g. ethanol.

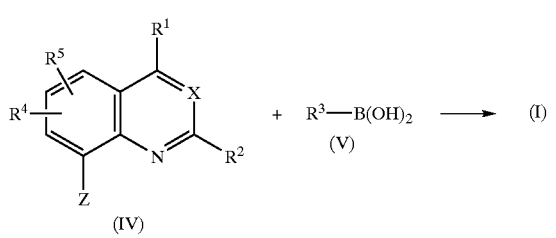

The above-mentioned Suzuki reaction, i.e. a palladium-catalyzed cross-coupling reaction of a phenylboronic acid derivative with a haloarene in the presence of a base, is extensively described in Suzuki A. et al. *Synthetic Communications*, 11:513–519, 1981 and Suzuki A., *Pure and Applied Chemistry*, 66, 213–222 (1994).

Compounds of formula (I-a), defined as compounds of formula (I) wherein $R^{1'}$ has the meaning of $R^1$ other than $C_{1-6}$alkyl, can be prepared by reacting an intermediate of formula (II) with an intermediate of formula (III). In intermediate (II), W is an appropriate leaving group such as halo, e.g. chloro, bromo, or a sulfonyloxy group, e.g. a mesyloxy or a tosyloxy group.

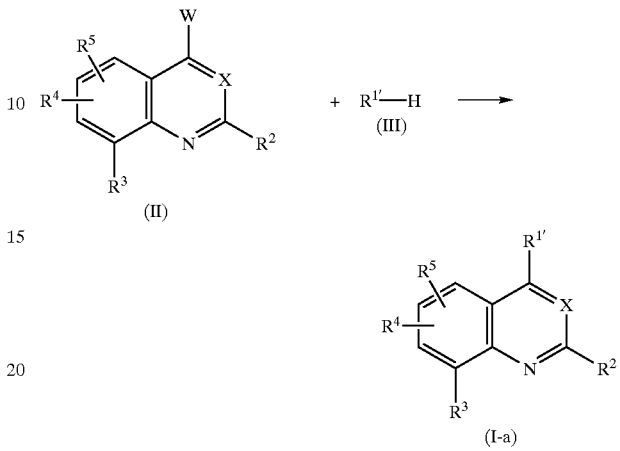

Said reaction can be performed in a reaction-inert solvent such as, for example, acetonitrile, N,N-dimethylformamide, methyl isobutylketone, tetrahydrofuran or dichloromethane; and in the presence of a suitable base such as, for example, sodium carbonate, sodium hydrogen carbonate or triethylamine. When the intermediates of formula (III) are volatile amines, said reaction may also be performed in a sealed reaction vial. Stirring may enhance the rate of the reaction. The reaction may conveniently be carried out at a temperature ranging between room temperature and reflux temperature.

Compounds of formula (I) wherein $R^1$ is $OR^7$, said compounds being represented by formula (I-b), may be prepared by O-alkylating an intermediate of formula (VI) with an intermediate of formula (VII), wherein $W^1$ is an appropriate leaving group such as halo, e.g. chloro, bromo, or a sulfonyloxy group, e.g. a mesyloxy or a tosyloxy group.

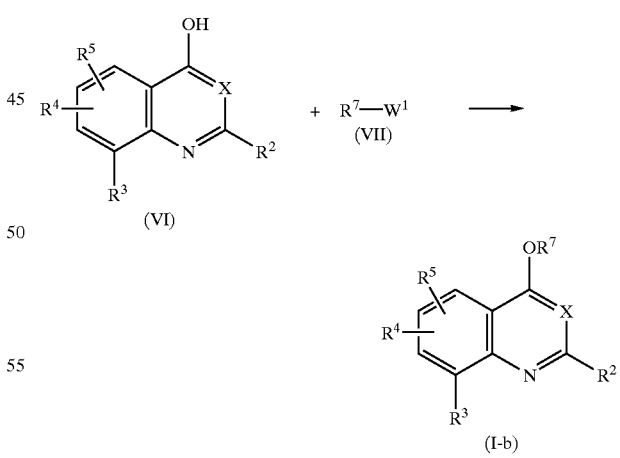

Said reaction for preparing compounds of formula (I-b) can be performed in a reaction-inert solvent such as, for example, N,N-dimethylformamide, and in the presence of a suitable base such as, for example, sodium hydride, preferably at a temperature ranging between room temperature and reflux temperature.

The compounds of formula (I) wherein $R^1$ is $-NHR^7$, represented by formula (I-c), can be prepared by N-alkylating an intermediate of formula (VIII) with an intermediate of formula $R^7$—W, wherein W is as previously defined. Compounds of formula (I-c) can be further N-alkylated with an intermediate of formula $R^6$—W, wherein W is as previously defined, yielding compounds of formula (I-d). These N-alkylations are conducted in a reaction-inert solvent such as, for example, an ether e.g. tetrahydofuran and preferably in the presence of a strong base, e.g. NaH.

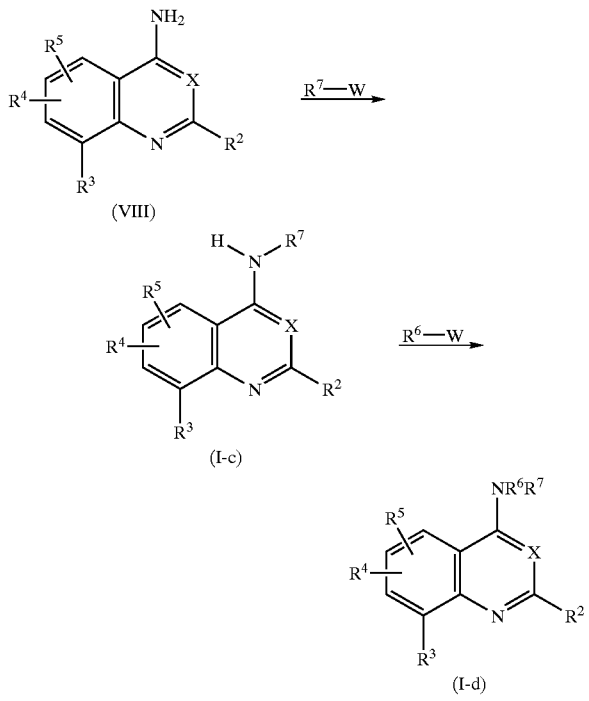

Compounds of formula (I-e), wherein X is CH and $R^{1''}$ and $R^{2'}$ are $C_{1-6}$alkyl, can be prepared by reacting an intermediate of formula (IX) with an intermediate of formula (XIII) and subsequent heating in concentrated sulfuric acid.

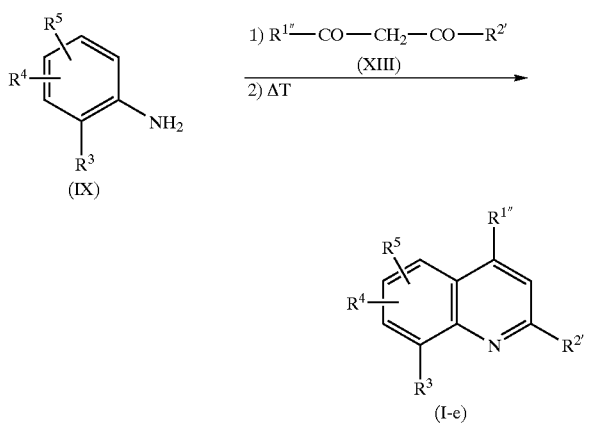

Further, compounds of formula (I) may also be converted into each other following art-known functional group transformation procedures.

Intermediates of formula (II) wherein X is CH, said intermediates being represented by formula (II-a), can be prepared as outlined herebelow in scheme I.

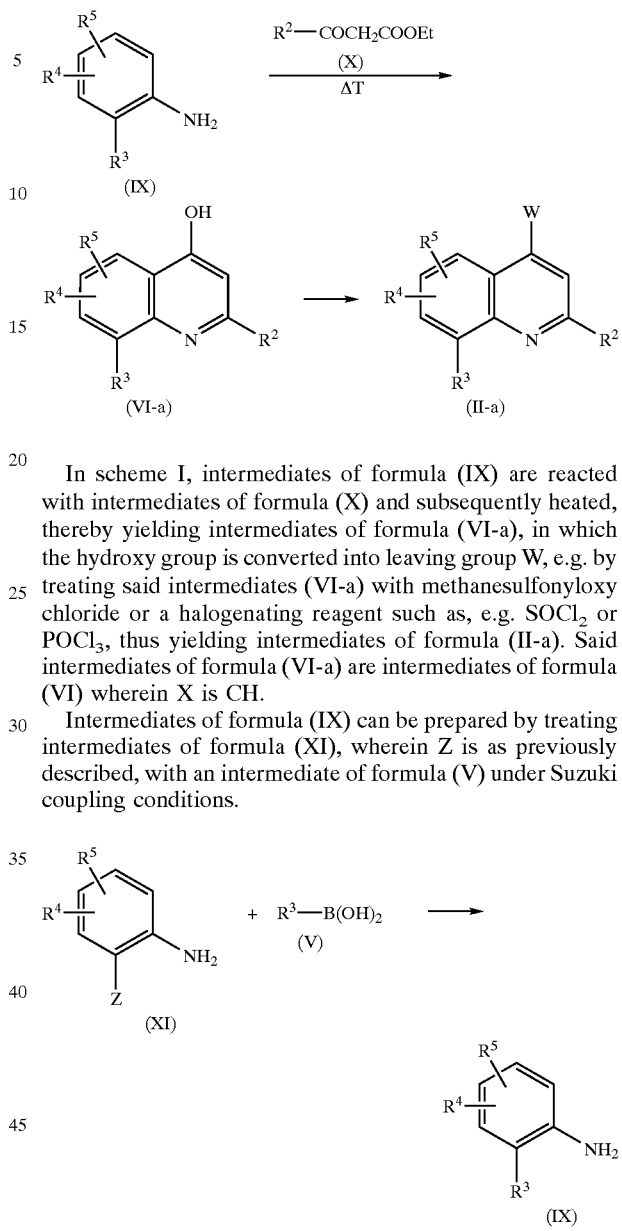

In scheme I, intermediates of formula (IX) are reacted with intermediates of formula (X) and subsequently heated, thereby yielding intermediates of formula (VI-a), in which the hydroxy group is converted into leaving group W, e.g. by treating said intermediates (VI-a) with methanesulfonyloxy chloride or a halogenating reagent such as, e.g. $SOCl_2$ or $POCl_3$, thus yielding intermediates of formula (II-a). Said intermediates of formula (VI-a) are intermediates of formula (VI) wherein X is CH.

Intermediates of formula (IX) can be prepared by treating intermediates of formula (XI), wherein Z is as previously described, with an intermediate of formula (V) under Suzuki coupling conditions.

Intermediates of formula (IX) can also be prepared by reacting an analogue of intermediate (XI) wherein the amino group is replaced by a nitro group, with intermediate (V) under Suzuki coupling conditions, and subsequent conversion of the nitro group to an amino group e.g. by hydrogenation using hydrogen gas and a suitable catalyst such as palladium-on-carbon.

Also, intermediates of formula (IX) can also be prepared by reacting an analogue of intermediate (XI) wherein the amino group is replaced by a carboxyl group, with intermediate (V) under Suzuki coupling conditions, and subsequent conversion of the carboxyl group to an amino group.

Intermediates of formula (IV) can generally be prepared by reacting an intermediate of formula (XII), wherein Z is as previously described, with an intermediate of formula (III). Said reaction can be performed as previously described for the synthesis of compounds of formula (I).

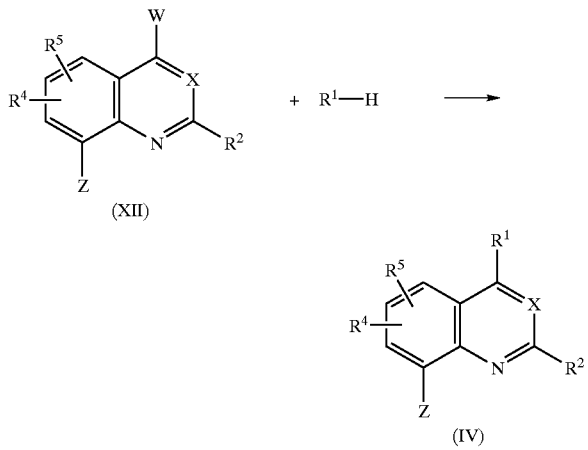

Intermediates of formula (VIII) are prepared by treating intermediates of formula (II) with ammonia.

Compounds of formula (I) and some of the intermediates may have one or more stereogenic centers in their structure, present in a R or a S configuration.

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g. [$^{125}$I]tyrosine CFR) to receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the IC$_{50}$ as the concentration of a compound necessary to displace 50% of the radiolabeled ligand from the receptor, and is reported as a "K$_i$" value calculated by the following equation:

$$K_i = \frac{IC_{50}}{1 + L/K_D}$$

where L=radioligand and K$_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)). With reference to CRF receptor binding affinities, CRF receptor antagonists of this invention have a K$_i$ of less than 10 μM. In a preferred embodiment of this invention, a CRF receptor antagonist has a K$_i$ of less than 1 μM, and more preferably less than 0.25 μM (i.e., 250 nM).

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder, that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorings, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

Hence, this invention provides the use of compounds of formula (I) for the manufacture of a medicine for treating physiological conditions or disorders arising from the hyper-secretion of corticotropin-releasing factor (CRF) and in particular for treating the disorders or illnesses mentioned above; and in a further embodiment the use of novel compounds of formula (I) as a medicine is provided.

The following examples are provided for purposes of illustration, not limitation.

EXPERIMENTAL PART

Hereinafter "THF" means tetrahydrofuran and "DCM" means dichloromethane.

A. Preparation of the Intermediates

EXAMPLE A.1 a) To a stirring solution of 2-bromoaniline (4.0 g) in 120 ml of toluene was added tetrakis(triphenylphosphine) palladium(0) (2.7 g, 2.33 mmol, 10% mol) and 2.0 M aqueous sodium carbonate solution (35 ml, 70 mmol). In a separate flask, dichlorobenzeneboronic acid (5.0 g) was dissolved in ethyl alcohol (35 ml). To the boronic acid solution was added the 2-bromoaniline mixture. The resulting mixture was heated to reflux overnight. The reaction mixture was cooled, diluted with ethyl acetate and washed with saturated ammonium chloride solution. The organic layer was dried, filtered, concentrated. The residue was purified by flash chromatography on silica gel yielding 2-amino-(2',4'-dichloro)biphenyl (intermediate (7)) (4.8 g). 300 MHz $^1$H NMR (CDCl$_3$): δ 3,54 (br s, 2H), 6.78 (d, 1H), 6.84 (d, 1H), 7.01 (d, 1H), 7.19–7.35 (m, 3H), 7.53 (d, 1H).

b) A solution of intermediate (7) (4.71 g), ethyl acetoacetate (2.58 g) and 20 mg of p-toluenesulfonic acid monohydrate in 100 ml of benzene was refluxed 30 minutes. The reaction mixture was cooled, concentrated and purified by flash chromatography on silica gel yielding intermediate (8) (4.5 g). 300 MHz $^1$H NMR (CDCl$_3$): δ 1.21 (t, 3H), 1.86 (s, 3H), 4.04 (q, 2H), 4.57 (s, 1H), 7.18 (s, 1H), 7.25–7.43 (m, 5H), 7.47 (d, 1H), 9.89 (s, 1H).

c) A solution of intermediate (8) (2.34 g) in 5 ml of diphenylether was added to 10 ml diphenylether at 240° C. and the solution was heated to reflux for 5 minutes. The reaction mixture was cooled and the solid was collected by filtration, and rinsed with diethyl ether, yielding 2-methyl-4-hydroxy-8-(2',4'-dichlorophenyl)quinoline (intermediate 9) as a white crystalline solid (1.33 g). 300 MHz $^1$H NMR (CDCl$_3$): δ 2.56 (s, 3H), 6.11 (s, 1H), 7.34–7.44 (m, 4H), 7.58 (d, 1H), 8.38 (d,1H), 8.82 (s, 1H).

d) A mixture of intermediate (9) (1.32 g) and phosphorous oxychloride (5 ml) was refluxed for 2 hours, cooled, poured onto ice and neutralized by 1N NaOH. The aqueous layer was extracted by ethyl acetate. The organic layer was washed with brine, dried, concentrated, yielding 2-methyl-4-chloro-8-(2',4'-dichlorophenyl)quinoline (intermediate 1) (1.31 mg). 300 MHz $^1$H NMR (CDCl$_3$): δ 2.58 (s, 3H), 7.34 (s, 2H), 7.39 (s,1H), 7.53 (s, 1H), 7.63–7.65 (m, 2H), 8.26 (dd,1H).

EXAMPLE A.2 a) A mixture of 2-amino-3-bromo-5 methyl benzoic acid (1 g) and formamide (0.6 ml) was placed in a 1 ml pressure vial and heated to 145° C. After heating for 1 hour, the vial was cooled to room temperature, and 50 ml water was added. The solid white mass was then filtered off and recrystallized from methanol, yielding intermediate (10) (1.01 g).

b) A mixture of intermediate (10) (1 g) was refluxed in 4 ml POCl$_3$ for 2 hours. After refluxing, the reaction was cooled and poured onto 50 ml ice. The aqueous solution was made basic with sodium bicarbonate and extracted with ethyl acetate. The organic layers were combined, dried and concentrated, yielding intermediate (11) which was used in the next step without purification.

c) Intermediate (11) was refluxed in the presence of 5 ml dipropyl amine for 1 hour. The reaction was diluted with water and extracted with ethyl acetate. The organic layer was combined, dried and concentrated, yielding a residue which was dissolved in ethylacetate and run through a plug of silica. Evaporation yielded intermediate (6) (0.4 g).

EXAMPLE A.3 a) A mixture of 4'-chloro-6-methoxy-2-biphenylcarboxylic acid (1.2 g), prepared according to the procedure of Meyers A. I. et al. in *J. Org. Chem.* 43:1372–1379 (1978), triethylamine (1.1 ml), diphenylphosphoryl azide (1.2 ml) and tert-butyl alcohol(80 ml) was placed in a 250 ml flask under nitrogen atmosphere. The solution was stirred and refluxed for 5 hours. After reflux, the reaction mixture was cooled and concentrated, yielding a residue which was suspended in diethyl ether. A solid by-product was filtered off and the mother liquid was concentrated, yielding 1.4 g of intermediate (12).

b) Intermediate (12) was dissolved in THF (60 ml), water (12 ml) and concentrated HCl (12 ml) and refluxed for 2 hours. The solution was concentrated and the residue was partitioned between ethyl acetate and water. The organic layer was separated, dried and concentrated, yielding intermediate (13).

c) Intermediate (13) was suspended in benzene (100 ml) in the presence of ethyl acetoacetate (2 ml) and refluxed using a dean stark trap for 3 hours. The reaction mixture was concentrated and the residue was added to an already hot solution (200° C.) of diphenyl ether (20 ml). This reaction mixture was allowed to stir for 15 minutes, cooled and slowly triturated with diethyl ether (200 ml), yielding intermediate (14).

c) Intermediate (14) (400 mg) was suspended in phosphorus oxychloride (2 ml) and heated to reflux for 2 hours. The reaction mixture was cooled and poured onto 100 ml of ice. The mixture was partitioned between ethyl acetate (200 ml) and an aqueous saturated sodium bicarbonate solution. The organic layer was separated, dried, an concentrated, yielding 4-chloro-7-methoxy-2-methyl-8-(4'-chlorophenyl) quinoline intermediate (5).

TABLE I-1

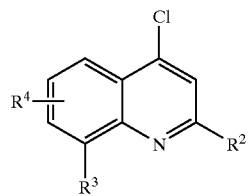

| Intm. No. | Ex. No. | $R^2$ | $R^4$ | $R^3$ |
|---|---|---|---|---|
| 1 | A.1 | $CH_3$ | H | 2,4-dichlorophenyl |
| 2 | A.1 | CH3 | H | 2,4,6-trimethylphenyl |
| 3 | A.1 | $CH_3$ | 7-$CH_3$ | 2-chlorophenyl |
| 4 | A.1 | $CH_3$ | 7-$CH_3$ | 2,4-dichlorophenyl |
| 5 | A.3 | $CH_3$ | 7-$CH_3O$ | 4-chlorophenyl |

TABLE I-2

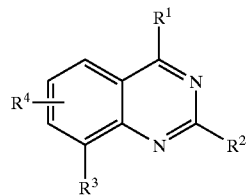

| Intm. No. | Ex. No. | $R^1$ | $R^2$ | $R^4$ | $R^3$ |
|---|---|---|---|---|---|
| 6 | A.2 | —$N(CH_2CH_2CH_3)_2$ | H | 7-$CH_3$ | Br |

B. Preparation of the Final Compounds

EXAMPLE B.1

A mixture of intermediate (1) (0.1 g) and p-toluenesulfonic acid monohydrate (160 mg) in 0.4 ml of dipropylamine in a 3 ml reacti-vials was refluxed at 180° C. for 48 hours. The reaction mixture was cooled, partitioned between ethyl acetate and water. The organic layer was washed with brine, dried, concentrated, purified on a preparative TLC plate (hexane/EtOAc, 10:1). Compound (1) was isolated as a pale yellow oil (80 mg).

EXAMPLE B.2

A solution of intermediate (1) (20 mg) in 0.5 ml of dimethylsulfoxide in a 1 ml reacti-vials was refluxed at 180° C. for 12 hours. The reaction mixture was cooled, partitioned between ethyl acetate and water. The organic layer was washed with brine, dried, concentrated, purified on a preparative TLC plate (hexane/EtOAc, 10:1). Compound (20) was isolated as a colorless oil.

EXAMPLE B.3

Intermediate (5) (0.4 g) and palladium tetraphenylphosphine (40 mg) were dissolved in 10 ml toluene and added to a solution of 2,4-dichlorophenyl boronic acid (490 mg) in ethanol (3 ml). To this was added a 2M solution of sodium carbonate (3 ml) and the resulting mixture was refluxed under nitrogen for 15 hours. After refluxing, the solution was cooled and extracted with diethyl ether (100 ml). The ether layer was dried, concentrated and purified on silica (1:9 ether:hexanes) yielding compound (19).

EXAMPLE B.4 a) A mixture of intermediate (7) (1.08 g), 2,4-pentanedione (908 mg) and calcium sulfate (2 g) was heated at 100° C. overnight. The reaction mixture was cooled and partitioned between ethyl acetate and water. The organic layer was washed with brine, dried, filtered and concentrated. The crude product was purified by flash chromatography on silica gel to provide 1.2 g (83%) of intermediate (15).

b) A solution of intermediate (15) (0.5 g) in concentrated sulphuric acid (5 ml) was heated overnight at 100° C. The reaction mixture was cooled and basified by adding 6N NaOH and extracted with ethyl acetate. The organic layer was washed with an aqueous saturated sodium bicarbonate solution, washed with brine, dried, filtered and evaporated. The residue was purified by flash chromatography on silica gel, yielding 0.4 g (85%) of 2,4-dimethyl-8-(2',4'-dichlorophenyl)quinoline (compound 22).

Table F-1 to F-2 list the intermediates that were prepared according to one of the above Examples and table F-3 lists the analytical data for these compounds.

TABLE F-1

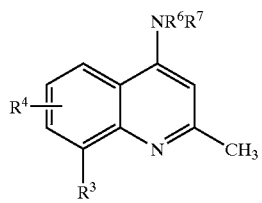

| Co. No | Ex. No. | R⁴ | R⁶ | R⁷ | R³ |
|---|---|---|---|---|---|
| 1 | B.1 | H | n-propyl | n-propyl | 2,4-dichlorophenyl |
| 2 | B.1 | H | n-propyl | cyclopropylmethyl | 2,4-dichlorophenyl |
| 3 | B.1 | H | n-propyl | n-propyl | phenyl |
| 4 | B.1 | H | n-propyl | cyclopropylmethyl | phenyl |
| 5 | B.1 | H | hydrogen | 3-heptyl | phenyl |
| 6 | B.1 | H | 2-methoxyethyl | 2-methoxyethyl | 2,4-dichlorophenyl |
| 7 | B.1 | H | ethyl | n-butyl | 2,4-dichlorophenyl |
| 8 | B.1 | H | n-propyl | phenyhnethyl | 2,4-dichlorophenyl |
| 9 | B.1 | H | n-propyl | n-propyl | 4-methoxyphenyl |
| 10 | B.1 | 7-CH₃O | n-propyl | n-propyl | 4-chlorophenyl |
| 11 | B.1 | 7-CH₃ | n-propyl | n-propyl | 2-chlorophenyl |
| 12 | B.1 | H | n-propyl | n-propyl | 4-methylphenyl |
| 13 | B.1 | 7-CH₃ | 2-methoxyethyl | 2-methoxyethyl | 2,4-dichlorophenyl |
| 14 | B.1 | 7-CH₃ | n-propyl | cyclopropylmethyl | 2,4-dicMorophenyl |
| 15 | B.1 | 7-CH₃ | n-propyl | n-propyl | 2,4-dichlorophenyl |
| 16 | B.1 | H | n-propyl | cyclopropylmethyl | 2,4,6-trimethylphenyl |
| 17 | B.1 | H | n-propyl | n-propyl | 2,4,6-trimethylphenyl |
| 18 | B.1 | H | 2-methoxyethyl | 2-methoxyethyl | 2,4,6-trimethylphenyl |
| 23 | B.1 | H | ethyl | n-butyl | 2,4,6-trimethylphenyl |
| 24 | B.1 | H | n-propyl | phenylmethyl | 2,4,6-trimethylphenyl |
| 25 | B.1 | H | n-propyl | n-butyl | 2,4,6-trimethylphenyl |
| 26 | B.1 | H | n-propyl | n-propyl | 4-trifluoromethylphenyl |
| 27 | B.1 | H | n-propyl | n-propyl | 4-chlorophenyl |
| 28 | B.1 | H | n-propyl | n-propyl | 2,6-dichloro-3-pyridinyl |
| 29 | B.1 | H | n-propyl | n-propyl | 6-dimethylarnino-2-chloro-3-pyridinyl |
| 30 | B.1 | H | n-propyl | n-propyl | 4,6-dimethoxyphenyl |
| 31 | B.1 | H | n-propyl | n-propyl | 2-dimethylamino-4-methyl-5-pyridinyl |
| 32 | B.1 | H | n-propyl | n-propyl | 2-dimethylamino-4,6-dimethyl-5-pyridinyl |

TABLE F-2

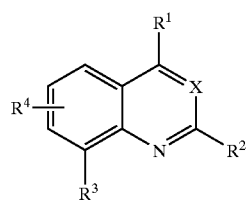

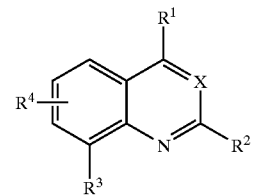

| Co. No. | Ex. No. | X | R¹ | R² | R⁴ | R³ |
|---|---|---|---|---|---|---|
| 19 | B.3 | N | —N(CH₂CH₂CH₃)₂ | H | 7-CH₃ | 2,4-dichloro-phenyl |
| 20 | B.2 | CH | —S—CH₃ | CH₃ | H | 2,4-dichloro-methyl |
| 21 | B.2 | CH | —OCH₃ | CH₃ | H | 2,4-dichloro-phenyl |
| 22 | B.4 | CH | —CH₃ | CH₃ | H | 2,4-dichloro-phenyl |

TABLE F-3

Analytical data

| Co. No. | ¹H NMR data (CDCl₃) | MS M⁺ |
|---|---|---|
| 1 | δ 0.89 (t, 6H), 1.56–1.66 (m, 4H), 2.52 (s, 3H), 3.25 (t, 4H), 6.73 (s,1H), 7.33 (d, 1H), 7.36 (d, 1H), 7.43 (d, 1H), 7.49 (d, 1H), 7.52 (s, 1H), 8.11 (d, 1H) | — |

TABLE F-3-continued

Analytical data

| Co. No. | $^1$H NMR data (CDCl$_3$) | MS M$^+$ |
|---|---|---|
| 2 | δ 0.07–0.08 (m, 2H), 0.47–0.50 (m, 2H), 0.92 (t, 3H), 0.95–1.05 (m, 1H), 1.58–1.66 (m, 2H), 2.53 (s, 3H), 3.20 (d, 2H), 3.40 (t, 2H), 6.80 (s, 1H), 7.33 (d, 1H), 7.36 (d, 1H), 7.40 (d, 1H), 7.49 (d, 1H), 7.52 (s, 1H), 8.14 (d, 1H) | — |
| 3 | δ 0.89 (t, 6H), 1.58–1.66 (m, 4H), 2.60 (s, 3H), 3.25 (t, 4H), 6.77 (s, 1H), 7.37–7.46 (m, 4H), 7.62 (d, 1H), 7.76 (d, 2H), 8.06 (d, 1H) | — |
| 4 | δ 0.07–0.09 (m, 2H), 0.47–0.50 (m, 2H), 0.92 (t, 3H), 0.95–1.05 (m, 1H), 1.58–1.66 (m, 2H), 2.61 (s, 3H), 3.20 (d, 2H), 3.39 (t, 2H), 6.84 (s, 1H), 7.37–7.49 (m, 4H), 7.64 (d, 1H), 7.77 (d, 2H), 8.09 (d, 1H) | — |
| 6 | δ 3.32 (s, 6H), 3.55 (t, 4H), 3.59 (t, 3H), 0.92 (t, 3H), 6.88 (s, 1H), 7.30 (d, 1H), 7.32 (d, 1H), 7.44 (t, 1H), 7.51 (s, 1H), 7.52 (d, 1H), 8.18 (d, 1H) | — |
| 7 | δ 0.87–0.92 (m, 6H), 1.15 (m., 2H)), 1.28–1.35 (m, 2H), 2.53 (s, 3H), 3.25 (t, 2H), 3.36 (q, 3H), 6.73 (s, 1H), 7.31 (d, 1H), 7.37 (d, 1H), 7.43 (t, 1H), 7.50 (d, 1H), 7.51 (s, 1H), 8.07 (d, 1H) | — |
| 9 | δ 0.88 (t, 6H), 1.57–1.62 (m, 4H), 2.60 (s, 3H), 3.23 (t, 4H), 3.88 (t, 3H), 6.76 (s, 1H), 7.01 (d, 2H), 7.42 (t, 1H), 7.61 (d, 1H), 7.72 (d, 2H), 8.02 (d, 1H) | — |
| 10 | δ 0.87 (t, 3H), 1.59–1.65 (m, 2H), 3.17 (t, 2H), 4.49 (s,2H), 6.73 (s, 1H), 7.28–7.34 (m, 6H), 7.35 (d, 1H), 7.42 (t, 1H), 7.52 (s, 1H), 7.53 (d, 1H), 8.20 (d, 1H) | — |
| 10 | δ 0.89 (m, 6H), 1.59–1.62 (m, 4H), 2.5 (s, 3H), 3.2 (m, 4H), 3.86 (t, 3 H), 6.64 (s, 1H), 7.26 (d, 1H), 7.44 (m, 4H), 8.05 (d, 1H) | — |
| 11 | δ 2.2 (s, 3H), 2.44 (s,3H), 6.66 (s, 1H), 7.26 (m, 1H), 7.33 (m, 3H), 7.5 (m, 1H), 7.98 (d,1H) | 366 |
| 14 | δ 2.20 (s, 3H), 2.44 (s, 3H), 6.66 (s, 1H), 7.26 (m, 1H), 7.33 (m, 3H), 7.5 (m, 1H), 7.98 (d, 1H) | — |
| 19 | — | 389 |
| 20 | δ 2.57 (s, 3H), 2.61 (s, 3H), 6.99 (s, 1H), 7.32–7.35 (m, 2H), 7.49–7.60 (m, 3H), 8.13 (d, 1H) | — |
| 22 | δ 2.55 (s, 3H), 2.61 (s,3H), 7.12 (s, 1H), 7.31 (d, 1H), 7.36 (d, 1H), 7.51 (s, 1H), 7.54 (t, 1H), 7.58 (d, 1H), 8.02 (d, 1H) | 301 |
| 23 | δ 0.92 (t, 3H), 1.18 (t, 3H), 1.33–1.38 (m, 2H), 1.58–1.64 (m, 2H), 1.91 (s, 3H), 2.38 (s, 3H), 2.52(s, 3H), 3.29 (t, 2H), 3.38 (q, 2H), 6.71 (s, 1H), 6.99 (s, 2H), 7.26 (s, 1H), 7.34 (d, 1H), 7.42 (t, 1H), 8.01 (d, 1H) | 360 |
| 24 | δ 0.88 (t, 3H), 1.63–1.68 (m, 2H), 1.92 (s, 6H), 2.38 (s, 3H), 2.49(s, 3H), 3.19 (t, 2H), 4.51 (s, 2H), 6.71 (s, 1H), 6.99 (s, 2H), 7.28–7.31 (m, 1H), 7.33–7.37 (m, 5H), 7.42 (dd, 1H), 8.13 (d, 1H) | 408 |
| 25 | δ 0.91 (t, 6H), 1.31–1.35 (m, 4H), 1.57–1.62 (m, 4H), 1.91 (s, 6H), 2.38 (s, 3H), 2.51 (s, 3H), 3.30 (t, 2H), 6.70 (s, 1H), 6.99 (s, 2H), 7.34 (d, 1H), 7.40 (dd, 1H), 8.01 (dd, 1H) | 388 |
| 26 | — | 386 |
| 27 | — | 352 |
| 28 | δ 0.89 (t, 6H), 1.56–1.66 (m, 4H), 2.61 (s, 3H), 3.26 (t, 4H), 6.80 (s, 1H), 7.45 (dd, 1H), 7.62 (dd, 1H), 7.69 (s, 2H), 8.14 (dd, 1H) | 388 |
| 29 | δ 0.88 (t, 6H), 1.56–1.64 (m, 4H), 2.62 (s, 3H), 3.13 (s, 6H), 3.26 (t, 4H), 6.77 (s, 1H), 6.84 (s, 1H), 6.90 (s, 1H), 7.43 (dd, 1H), 7.63 (d, 1H), 8.08 (d, 1H) | 396 |
| 30 | δ 1.61 (m, 4H), 2.53 (s, 3H), 3.22 (t, 4H), 3.73 (s, 3H), 3.88 (s, 3H), 6.62 (s, 1H), 6.71 (s, 1H), 7.38 (m, 4H), 7.58 (dd, 1H), 8.04 (dd, 1H) | — |
| 31 | δ 0.88 (t, 6H), 1.61 (m, 4H), 2.06 (s, 3H), 2.53 (s, 3H), 3.13 (s, 6H), 3.22 (t, 4H), 6.47 (s, 1H), 6.72 (s, 1H), 7.42 (m, 2H), 8.04 (dd, 1H), 8.09 (dd, 1H) | — |
| 32 | δ 1.63 (m, 4H), 1.89 (s, 3H), 2.07 (s, 3H), 2.50 (s, 3H), 3.13 (s, 6H), 3.22 (t, 4H), 6.39 (s, 1H), 6.72 (s, 1H), 7.40 (m, 2H), 8.04 (d, 1H) | — |

C. Pharmacological Examples

EXAMPLE C.1

CRF Receptor Binding Activity

Compounds were evaluated for binding activity to the CRF receptor by a standard radioligand binding assay as generally described by DeSouza et al. (*J. Neurosci.* 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay was performed in 1.5 ml Eppendorf tubes using approximately $1 \times 10^6$ cells per tube stably transfected with human CRF receptors. Each tube received about 0.1 ml of assay buffer (e.g., Dulbecco's phosphate buffered saline, 10 mM magnesium chloride, 20 $\mu$M bacitracin) with or without unlabeled sauvagine, urotensin I or CRF (final concentration, 1 $\mu$M) to determine nonspecific binding, 0.1 ml of [125I] tyrosine-ovine CRF (final concentration approximately 200 pM or approximately the $K_D$ as determined by Scatchard analysis) and 0.1 ml of a membrane suspension of cells containing the CRF receptor. The mixture was incubated for 2 hours at 22° C. followed by the separation of the bound and free radioligand by centrifugation. Following two washes of the pellets, the tubes were cut just above the pellet and monitored in a gamma counter for radioactivity at approximately 80% efficiency. All radioligand binding data was analyzed using a non-linear least-square curve-fitting program.

Binding activity corresponds to the concentration (nM) of the compound necessary to displace 50% of the radiolabeled ligand from the receptor. Compounds 1, 2, 4, 6–11, 20 and 21 were found to have a $K_i \leq 250$ nM.

What is claimed is:

1. A compound of formula:

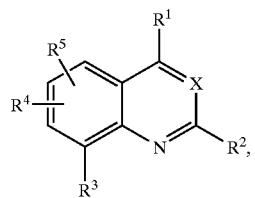

(I)

including the stereoisomers or the pharmaceutically acceptable acid addition salt forms thereof, wherein X is CH;

$R^1$ is $C_{1-6}$alkyl, $NR^6R^7$, $OR^7$ or $SR^7$;

$R^2$ is $C_{1-6}$alkyl, $C_{1-6}$alkyloxy or $C_{1-6}$alkylthio;

$R^3$ is $Ar^1$ or $Het^1$;

$R^4$ and $R^5$ are each independently selected from hydrogen, halo, $C_{1-6}$alkyl, $C_{1-6}$alkyloxy, trifluoromethyl, cyano, nitro, amino, and mono- or di($C_{1-6}$ alkyl)amino;

$R^6$ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy$C_{1-6}$alkyl;

$R^7$ is $C_{1-8}$alkyl, mono- or di($C_{3-6}$cycloalkyl)methyl, $Ar^2CH_2$, $C_{1-6}$alkyloxy-$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, mono- or di($C_{1-6}$alkyl)amino$C_{1-6}$alkyl, di($C_{1-6}$alkyl)amino, $C_{1-6}$alkylcarbonyl$C_{1-6}$alkyl;

or $R^6$ and $R^7$ taken together with the nitrogen atom to which they are attached may form a pyrrolidinyl, piperidinyl, homopiperidinyl or morpholinyl group, optionally substituted with $C_{1-6}$alkyl or $C_{1-6}$alkyloxy$C_{1-6}$alkyl; and $Ar^1$ is phenyl; phenyl substituted with 1, 2 or 3 substituents each independently selected from halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl)amino;

$Het^1$ is pyridinyl; pyridinyl substituted with 1, 2 or 3 substituents each independently selected from halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl)amino; and $Ar^2$ is phenyl; phenyl substituted with 1, 2 or 3 substituents each independently selected from halo, $C_{1-6}$ alkyl, $C_{1-6}$alkyloxy, di($C_{1-6}$alkyl)amino$C_{1-6}$alkyl, trifluoromethyl;

with the proviso that 2,4-dimethyl-8-(2-nitrophenyl)-quinoline is not included.

2. A compound according to claim 1 wherein $R^1$ is $OR^7$ or $SR^7$ and $R^7$ is $C_{1-6}$alkyl; or $R^1$ is $NR^6R^7$ and $R^6$ is hydrogen or $C_{1-6}$alkyl, and $R^7$ is $C_{1-6}$alkyl or $C_{3-6}$cycloalkylmethyl; $R^2$ is $C_{1-6}$alkyl; $R^3$ is a phenyl substituted with 1, 2 or 3 substituents each independently selected from $C_{1-6}$alkyl, $C_{1-6}$alkyloxy or halo, or $R^3$ is a pyridinyl substituted with 1, 2 or 3 substituents each independently selected from $C_{1-6}$alkyl or di($C_{1-6}$alkyl)amino; and $R^4$ or $R^5$ are each independently selected from hydrogen or $C_{1-6}$alkyl.

3. A compound according to claim 1 wherein $R^1$ is $NR^6R^7$ wherein $R^6$ is $C_{2-4}$alkyl and $R^7$ is $C_{2-4}$alkyl or cyclopropylmethyl; $R^2$ is $C_{1-2}$alkyl; $R^3$ is phenyl substituted with 1, 2 or 3 substituents each independently selected from hydrogen, halo or $C_{1-6}$alkyl.

4. A compound according to claim 1 wherein $R^1$ is $NR^6R^7$ wherein $R^6$ is $C_{3-4}$alkyl and $R^7$ is $C_{3-4}$alkyl or cyclopropylmethyl; $R^2$ is methyl; $R^3$ is 3-pyridinyl substituted on the 4- and/or 6-position with methyl or dimethylamino.

5. A compound according to claim 1 wherein the compound is 2-methyl-4-dipropylamino-8-(2',4'-dichlorophenyl)-quinoline; or 2-methyl-4-(N-propyl-N-cyclopropanemethyl)amino-8-(2',4'-dichlorophenyl)-quinoline; a stereoisomeric form or a pharmaceutically acceptable acid addition salt thereof.

6. A composition comprising a pharmaceutically acceptable carrier, and as active ingredient a therapeutically effective amount of a compound as claimed in claim 1.

7. A process for preparing a composition wherein a therapeutically effective amount of a compound as claimed in claim 1 is intimately mixed with a pharmaceutically acceptable carrier.

8. A compound of Formula (II-a)

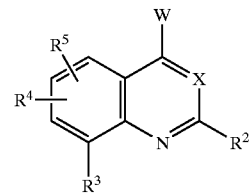

(II-a)

or a stereoisomeric form or an acid addition salt thereof wherein

X is CH;

$R^2$ is $C_{1-6}$alkyl, $C_{1-6}$alkyloxy or $C_{1-6}$alkylthio;

$R^3$ is $Ar^1$ or $Het^1$;

$R^4$ and $R^5$ are each independently hydrogen, halo, $C_{1-6}$alkyl, $C_{1-6}$alkyloxy, trifluoromethyl, cyano, nitro, amino, or mono- or di($C_{1-6}$alkyl)amino;

$Ar^1$ is phenyl; phenyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl) amino;

$Het^1$ is pyridinyl; pyridinyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl) amino; and W is halo, mesyloxy or toxyloxy.

9. A method for treating an endocrine, psychiatric or neurologic disorder or illness in a warm-blooded animal comprising administering to said animal in need of treatment a therapeutically effective amount of a compound of the formula:

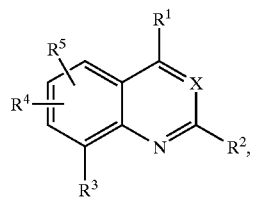

including the stereoisomers or the pharmaceutically acceptable acid addition salt forms thereof, wherein X is CH;

$R^1$ is $C_{1-6}$alkyl, $NR^6R^7$, $OR^7$ or $SR^7$;

$R^2$ is $C_{1-6}$alkyl, $C_{1-6}$alkyloxy or $C_{1-6}$alkylthio;

$R^3$ is $Ar^1$ or $Het^1$;

$R^4$ and $R^5$ are each independently hydrogen, halo, $C_{1-6}$alkyl, $C_{1-6}$alkyloxy, trifluoromethyl, cyano, nitro, amino, or mono- or di($C_{1-6}$alkyl)amino;

$R^6$ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy-$C_{1-6}$alkyl;

$R^7$ is $C_{1-8}$alkyl, mono- or di($C_{3-6}$cycloalkyl)methyl, $Ar^2CH_2$, $C_{1-6}$alkyloxy-$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, mono- or di($C_{1-6}$alkyl)amino-$C_{1-6}$alkyl, di($C_{1-6}$alkyl)amino, or $C_{1-6}$-alkylcarbonyl-$C_{1-6}$alkyl;

or $R_6$ and $R_7$ taken together with the nitrogen atom to which they are attached form a pyrrolidinyl, piperidinyl, homopiperidinyl or morpholinyl group, optionally substituted with $C_{1-6}$alkyl or $C_{1-6}$alkyloxy$C_{1-6}$alkyl; and $Ar^1$ is phenyl; phenyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl)amino;

$Het^1$ is pyridinyl; pyridinyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl)amino; and $Ar^2$ is phenyl; phenyl substituted with 1, 2 or 3 substituents each independently selected from the group consisting of halo, $C_{1-6}$alkyl, $C_{1-6}$alkyloxy, di($C_{1-6}$alkyl)amino$C_{1-6}$alkyl, and trifluoromethyl.

10. A process of preparing a compound of formula (I) as claimed in claim 1 wherein a) intermediates of formula (IV) are reacted with intermediates of formula (V) under Suzuki coupling conditions;

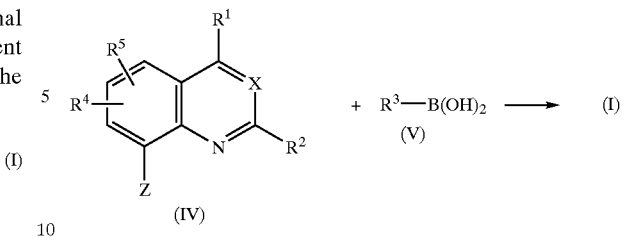

b) an intermediate of formula (II) is reacted with an intermediate of formula (III), wherein $R^{1'}$ has the meaning of $R^1$ other than $C_{1-6}$alkyl, thereby yielding compounds of formula (I-a);

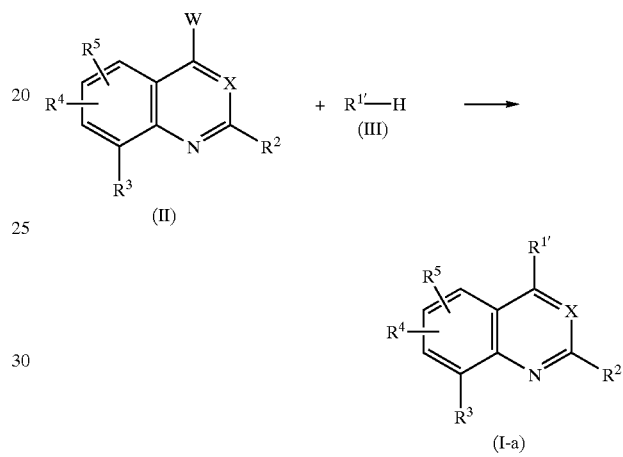

c) an intermediate of formula (VI) is O-alkylated with an intermediate of formula (VIIX) in a reaction-inert solvent and in the presence of a suitable base, yielding compounds of formula (I-b), defined as compounds of formula (I) wherein $R^1$ is $OR^7$,

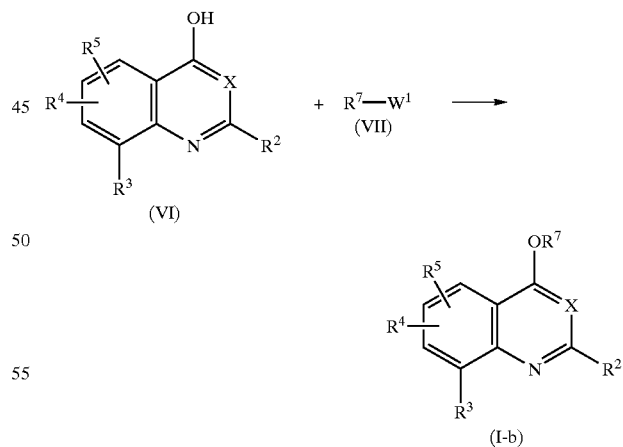

wherein in the above reaction schemes the radicals $R^1$, $R^2$, $R^3$, $R^6$, $R^7$ and X are as defined in claim 1, Z is bromo or iodo and W and $W^1$ are appropriate leaving groups;

or, if desired, compounds of formula (I) are converted into each other following art-known transformation reactions; and further, if desired, compounds of formula (I) are converted into an acid addition salt by treatment with an acid, or conversely, the acid addition salt forms are converted into the free base by treatment with alkali; and, if desired, preparing stereochemically isomeric forms thereof.

11. A method of antagonizing a CRF receptor in a warm-blooded animal comprising administering to the animal an effective amount of a compound of the formula:

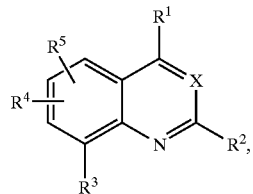

(I)

including the stereoisomers or the pharmaceutically acceptable acid addition salt forms thereof, wherein X is CH;

$R^1$ is $C_{1-6}$alkyl, $NR^6R^7$, $OR^7$ or $SR^7$;

$R^2$ is $C_{1-6}$-alkyl, $C_{1-6}$alkyloxy or $C_{1-6}$alkylthio;

$R^3$ is $Ar^1$ or $Het^1$;

$R^4$ and $R^5$ are each independently hydrogen, halo, $C_{1-6}$alkyl, $C_{1-6}$alkyloxy, trifluoromethyl, cyano, nitro, amino, or mono- or di($C_{1-6}$alkyl)amino;

$R^6$ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy-$C_{1-6}$alkyl;

$R^7$ is $C_{1-8}$alkyl, mono- or di($C_{3-6}$cycloalkyl)methyl, $Ar^2CH_2$, $C_{1-6}$alkyloxy$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, mono- or di($C_{1-6}$alkyl)amino-$C_{1-6}$alkyl, di($C_{1-6}$alkyl)amino, or $C_{1-6}$alkylcarbonyl $C_{1-6}$alkyl;

or $R_6$ and $R_7$ taken together with the nitrogen atom to which they are attached form a pyrrolidinyl, piperidinyl, homopiperidinyl or morpholinyl group, optionally substituted with $C_{1-6}$alkyl or $C_{1-6}$alkyloxy$C_{1-6}$alkyl; and $Ar^1$ is phenyl; phenyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl)amino;

$Het^1$ is pyridinyl; pyridinyl substituted with 1, 2 or 3 substituents each independent selected from the group consisting of halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl)amino; and $Ar^2$ is phenyl; phenyl substituted with 1, 2 or 3 substituents each independently selected from the group consisting of halo, $C_{1-6}$alkyl, $C_{1-6}$alkyloxy, di($C_{1-6}$alkyl)amino $C_{1-6}$alkyl, and trifluoromethyl.

12. A method of treating a disorder manifesting hypersecretion of CRF in a warm-blooded animal comprising administering to the animal an effective amount of a compound of the formula:

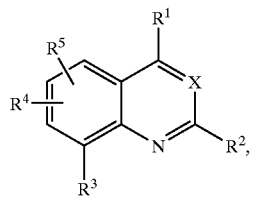

(I)

including the stereoisomers or the pharmaceutically acceptable acid addition salt forms thereof, wherein X is CH;

$R^1$ is $C_{1-6}$alkyl, $NR^6R$, $OR^7$ or $SR^7$;

$R^2$ is $C_{1-4}$alkyl, $C_{1-6}$alkyloxy or $C_{1-6}$alkylthio;

$R^3$ is $Ar^1$ or $Het^1$;

$R^4$ and $R^5$ are each independently hydrogen, halo, $C_{1-6}$alkyl, $C_{1-6}$alkyloxy, trifluoromethyl, cyano, nitro, amino, or mono- or di($C_{1-6}$alkyl)amino;

$R^6$ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy-$C_{1-6}$ alkyl;

$R^7$ is $C_{1-8}$alkyl, mono- or di($C_{3-6}$cycloalkyl)methyl, $Ar^2CH_2$, $C_{1-6}$alkyloxy$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, mono- or di($C_{1-6}$alkyl)amino-$C_{1-6}$alkyl, di($C_{1-6}$alkyl)amino, or $C_{1-6}$alkylcarbonyl $C_{1-6}$alkyl;

or $R_6$ and $R_7$ taken together with the nitrogen atom to which they are attached form a pyrrolidinyl, piperidinyl, homopiperidinyl or morpholinyl group, optionally substituted with $C_{1-6}$alkyl or $C_{1-6}$alkyloxy$C_{1-6}$alkyl; and $Ar^1$ is phenyl; phenyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl)amino;

$Het^1$ is pyridinyl; pyridinyl substituted with 1, 2 or 3 substituents each independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl) amino; and $Ar^2$ is phenyl; phenyl substituted with 1, 2 or 3 substituents each independently selected from the group consisting of halo, $C_{1-6}$alkyl, $C_{1-6}$alkyloxy, di($C_{1-6}$alkyl) amino $C_{1-6}$alkyl, and trifluoromethyl.

13. The method of claim 12 wherein the disorder is selected from depression, an anxiety-related disorder, a feeding disorder, stress-induced immune suppression, stroke, Cushing's disease, infantile spasms, epilepsy, seizure, an inflammatory condition.

14. The method of claim 13 wherein the feeding disorder is anorexia nervosa, bulimia or irritable bowel syndrome.

* * * * *